United States Patent [19]
Josten et al.

[11] Patent Number: 5,973,173
[45] Date of Patent: Oct. 26, 1999

[54] PROCESS FOR CONCENTRATING AZELAIC ACID

[75] Inventors: Horst Josten, Duesseldorf; Wilhelm Johannisbauer, Erkrath; Manfred Lindemann, Solingen, all of Germany; Dennis G. Gaige, Fairfield; Kenneth R. McVay, Hamilton, both of Ohio

[73] Assignee: Henkel Kommanditgesellschaft auf Aktien, Duesseldorf, Germany

[21] Appl. No.: 08/844,804

[22] Filed: Apr. 22, 1997

Related U.S. Application Data

[63] Continuation of application No. 08/452,207, May 26, 1995, abandoned.

[51] Int. Cl.⁶ .................................................... C11B 3/12
[52] U.S. Cl. .................... 554/207; 554/206; 554/132; 554/133; 203/98
[58] Field of Search .................... 584/181, 182, 584/183, 204, 207, 132, 206, 133; 203/98

[56] References Cited

U.S. PATENT DOCUMENTS 3,402,108   9/1968   Oehlschlaeger et al. ................ 203/31

*Primary Examiner*—Deborah D. Carr
*Attorney, Agent, or Firm*—Ernest G. Szoke; Wayne C. Jaeschke; Daniel S. Ortiz

[57] ABSTRACT

Pure azelaic acid is obtained by working up a reaction mixture containing $C_{1-18}$ monocarboxylic acids, mainly pelargonic acid, and $C_{4-16}$ dicarboxylic acids, mainly azelaic acid, obtained from the ozonolysis of oleic acid or a starting mixture containing oleic acid. All but <2% by weight of the monocarboxylic acids and part of the dicarboxylic acids with a chain length of $<C_9$ and $>C_9$ are separated off to obtain a prepurified product containing more than 75% by weight of oleic acid and the prepurified product is concentrated to more than 90% by weight of oleic acid in several process steps. In a first process step (1), the dicarboxylic acids with chain lengths of $<C_9$ present in the prepurified product are removed as first runnings by fractional distillation. In a second process step (2), the bottom product obtained is reacted with water to split carboxylic anhydrides present in the bottom product. In a third process step (3), the reaction mixture is subjected to overhead distillation. The third process step (3) is carried out after or at the same time as the second process step (2). The product yield is improved. The process is particularly suitable for working on an industrial scale.

24 Claims, 1 Drawing Sheet

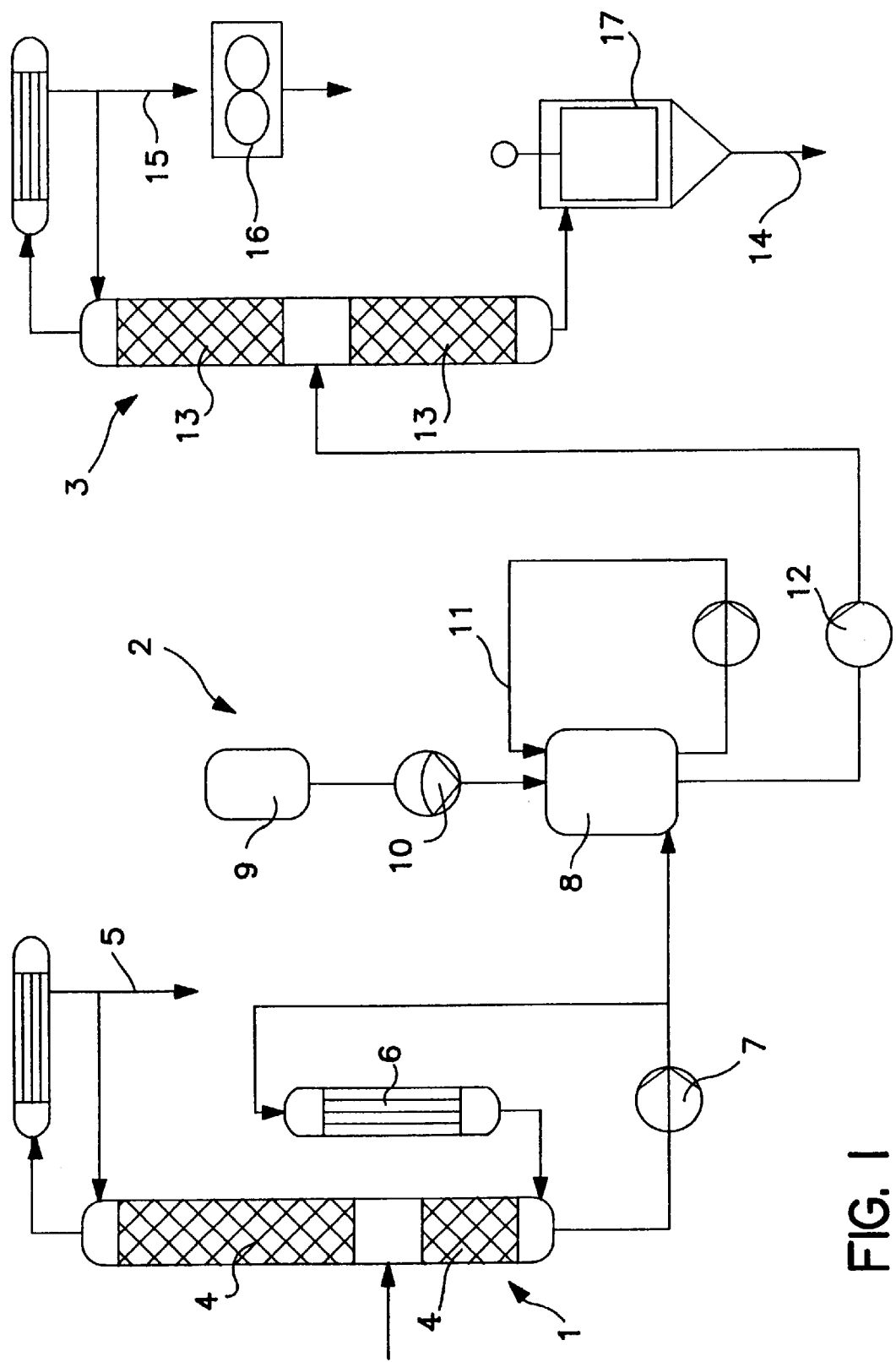
FIG. I

PROCESS FOR CONCENTRATING AZELAIC ACID

This application is a continuation of 08/452,207 filed May 26, 1995, now abandoned.

FIELD OF THE INVENTION

This invention relates to a process for the production of azelaic acid by working up a reaction mixture containing $C_{1-18}$ monocarboxylic acids, mainly pelargonic acid, and $C_{4-16}$ dicarboxylic acids, mainly azelaic acid, obtained from the ozonolysis of oleic acid or a starting mixture containing oleic acid. In this process, all but <2% by weight of the monocarboxylic acids and part of the dicarboxylic acids with a chain length of <$C_9$ and >$C_9$ are separated off to obtain a prepurified product containing more than 75% by weight of azelaic acid and the prepurified product is concentrated to more than 90% by weight of azelaic acid in several process steps of which the last is an overhead distillation step.

Azelaic acid is a saturated aliphatic $C_9$ dicarboxylic acid which is also known as nonanedioic acid or heptane dicarboxylic acid. Azelaic acid is a commercial product which is used as a starting material for the production of alkyd resins, polyesters, plasticizers and lubricants.

RELATED ART

Azelaic acid is prepared by ozonolysis of oleic acid. Pelargonic acid ($C_9$ monocarboxylic acid) is formed as a secondary product and is also recovered as a useful material in the working up of the reaction mixture. The process for the production of azelaic acid is described, for example, in U.S. Pat. No. 2,813,113.

The reaction mechanism is complex and the oleic acid feed to the process usually contains saturated higher fatty acids ($C_{14}$ to $C_{18}$), polyunsaturated acids and isomeric monounsaturated $C_{18}$ acids. Accordingly, in addition to the desired azelaic acid, the reaction product contains a number of other acids, mainly $C_{1-18}$ monocarboxylic acids and $C_{4-16}$ dicarboxylic acids. Azelaic acid is recovered from this mixture in a concentration of more than 90% by weight by a complicated working-up process.

One such process is described in U.S. Pat. No. 3,402,108. The reaction product obtained from the ozonolysis of oleic acid is subjected to distillation to reduce both the hydrocarbon content and to remove the monocarboxylic acids with chain lengths up to $C_9$, including the relatively large percentage of pelargonic acid. The dicarboxylic acids are distilled off from the residue of the first distillation step together with the remaining monocarboxylic acids with chain lengths of >$C_9$. The product obtained from this overhead distillation is then treated with hot water in an extraction step. A hot aqueous solution of the water-soluble dicarboxylic acids together with a small percentage of water-insoluble monocarboxylic acids is obtained. After drying of the aqueous solution, azelaic acid is obtained in a purity of more than 80% by weight.

Other working-up steps are then carried out to obtain azelaic acid in the required purity of more than 90% by weight. After bleaching with ozone-containing oxygen, the remaining monocarboxylic acids are extracted with a non-polar hydrocarbon, for example octane. The raffinate is crystallized and the azelaic acid crystals are filtered off, washed and dried. For further purification, the dry filter cake is distilled overhead.

This known working-up process gives an azelaic acid with a purity of more than 90% by weight and with a percentage content of monocarboxylic acids of less than 0.05% by weight. However, it is desirable to improve the product yield of this known process. In particular, the selectivity of the filtration step is poor. This is reflected in the fact that the mother liquor removed during the filtration step still contains around 40% by weight of the non-volatile portion, of azelaic acid.

Another objective is to replace the crystallization step by process steps which are more suitable for carrying out the working-up process on an industrial scale.

Accordingly, the problem addressed by the present invention was to improve the product yield of the process mentioned at the beginning and also its suitability for working on an industrial scale.

BRIEF DESCRIPTION OF THE INVENTION

According to the invention, the solution to this problem is a process wherein in a first process step, the dicarboxylic acids with chain lengths of <$C_9$ present in the prepurified product are removed as first runnings by fractional distillation; in a second process step, the bottom product obtained is reacted with water to split carboxylic anhydrides present in the bottom product and, in the third process step, the reaction mixture is subjected to overhead distillation. The third process step is carried out after or at the same time as the second process step.

Accordingly, the process according to the invention retains the working-up steps of the reaction mixture from the ozonolysis of oleic acid up to and including the extraction of the monocarboxylic acids with a non-polar hydrocarbon. According to the invention, however, the following vacuum crystallization and subsequent filtration steps of the prior art are replaced by fractional distillation and subsequent splitting of the anhydrides formed in the fractional distillation step. As in the prior art, the final step is an overhead distillation to remove the relatively long-chain dicarboxylic acids.

The improved working-up process in accordance with the invention has several advantages. It requires fewer working-up steps than the known process. Thus, there is no longer any need for the vacuum crystallization, the subsequent filtration to remove the azelaic acid crystals, the washing of the crystals and the drying of the moist filter cake. According to the invention, these working-steps are replaced by fractional distillation and subsequent splitting of the carboxylic anhydrides.

The product yield is considerably better than in the prior art for two reasons. Firstly, the crystallization and filtration steps, which led to considerable losses of azelaic acid, are no longer necessary. Secondly, splitting of the carboxylic anhydrides enables the azelaic acid, which has reacted to form azelaic anhydrides at the elevated temperatures prevailing in the distillation steps, to be recovered.

In addition, the destruction of the long-chain anhydrides formed through exposure of the dicarboxylic acids to high temperatures during the fractionation step is crucial to the invention. By feeding in water after the first fractionation step, the anhydrides are split and the original dicarboxylic acids are reformed therefrom. Through this measure, the product yield of the process according to the invention can be considerably increased in relation to the known working-up process.

Finally, fractional distillation can be carried out more economically on an industrial scale than crystallization and filtration. Accordingly, the two-stage fractionation according to the invention considerably simplifies the process as a whole.

Another advantage lies in the possibility of obtaining azelaic acid with a far higher purity than 90% by weight.

BRIEF DESCRIPTION OF THE DRAWINGS

The FIGURE is a schematic representation of the process of the invention.

DETAILED DESCRIPTION OF THE INVENTION

The first and/or third process steps are preferably carried out in a fractionating column under a head pressure of 1 to 30 mbar.

In the interests of moderate temperature evaporation, a falling-film evaporator is used as the "bottom" heater in the first process step.

In the interests of moderate temperature evaporation in the third process step, a thin-layer evaporator with a rotating wiper (wiped-film evaporator) or a falling-film evaporator is preferably used as the "bottom" heater.

Splitting of the anhydrides may be carried out in various ways. In one advantageous embodiment of the invention, the second step of the process is carried out in a stirred tank reactor, more particularly with forced circulation, or in a static mixer. In one particularly advantageous embodiment, the bottom product obtained in the first process step is fed directly into the fractionating column (second column) used to carry out the third process step and, at the same time, steam is introduced into that column to carry out the second process step. Accordingly, the second and third process steps are carried out simultaneously in the same column which further simplifies the process as a whole.

In this case, it is further proposed that the bottom product obtained in the first process step be introduced substantially in the middle of the second column and that the steam, more particularly superheated steam, be introduced into the evaporator of the second column. Accordingly, the steam is passed through the column packing in countercurrent to the boiling liquid mixture.

One example of embodiment of the invention is described in detail in the following with reference to the accompanying drawing, wherein FIG. 1 is a flow chart of the first to third steps of the process which follow the extraction stages known from the prior art. In the process illustrated in FIG. 1, the prepurified azelaic acid is concentrated from around 80% by weight to high purity, normally to more than 90% by weight, in only one pass.

FIG. 1 shows two fractionating columns 1, 3 with a reaction stage 2 in between.

The starting mixture introduced into the fractionating column 1 had the composition shown in Table 1:

TABLE 1

Composition of the prepurified product

| Component | % by weight |
| --- | --- |
| $C_9$ Monocarboxylic acid (pelargonic acid) | 0.1 |
| $C_5$ Dicarboxylic acid | 1.1 |
| $C_6$ Dicarboxylic acid | 2.2 |
| $C_7$ Dicarboxylic acid | 2.6 |
| $C_8$ Dicarboxylic acid | 4.2 |
| $C_9$ Dicarboxylic acid (azelaic acid) | 79.0 |
| $C_{10}$ Dicarboxylic acid | 2.4 |
| $C_{11}$ Dicarboxylic acid | 5.2 |
| $C_{12}$ Dicarboxylic acid | 0.5 |

TABLE 1-continued

Composition of the prepurified product

| Component | % by weight |
| --- | --- |
| $C_{13}$ Dicarboxylic acid | 0.4 |
| Unknowns | 2.3 |
| | 100.0 |

The prepurified product is introduced into the middle of the first fractionating column 1 which is operated in vacuo and which is equipped with a low-pressure-loss mass transfer packing 4. In this fractionating stage, first runnings 5 are removed at a high reflux ratio, the dicarboxylic acids with chain lengths of up to $C_9$ being removed to the extent necessary to obtain the required azelaic acid purity.

The column 1 operates at a low head pressure, preferably of 1 to 30 mbar. Hydraulically, it is designed in such a way that the pressure loss is between 2 and 20 mbar. A falling film evaporator 6 is preferably used for moderate evaporation.

The bottom product of the first fractionation is pumped by a pump 7 into a holding tank 8 with forced circulation 11 where it is in contacted with water delivered from a tank 9 by a pump 10. The low-volatility carboxylic anhydrides formed by exposure to high temperatures in the evaporator 6 and in the other preceding process stages are thus split into the original dicarboxylic acids.

A stirred tank reactor is used as the holding tank 8. Alternatively, a static mixer may be provided.

After the reaction, the mixture is pumped by a pump 12 into the middle of a second fractionating column 3 which is also operated in vacuo and equipped with a low-pressure-loss mass transfer packing 13. In the second fractionating column 3, the mixture is distilled overhead at a low reflux ratio, a residue 14 being removed in the quantity necessary to achieve the required azelaic acid purity. The concentrated azelaic acid accumulating as distillate 15 is delivered to a flaking roller 16 on which it is converted into flakes by cooling below its melting point.

The column 3 is preferably operated at a head pressure of 1 to 30 mbar. Hydraulically, it is designed in such a way that the pressure loss is between 2 and 20 mbar. A wiped-film evaporator 17 or a falling film evaporator is preferably used for moderate evaporation.

EXAMPLES

The mode of operation of the process for concentrating azelaic acid was demonstrated in several tests carried out in the experimental installation diagrammatically illustrated in FIG. 1. The installation consisted of two fractionating columns 1, 3 arranged in tandem with a stirred tank 8 in between.

The first column 1 had a diameter of 348 mm and was equipped with a 3860 mm long Sulzer BX woven packing of stainless steel (2180 mm for the concentrating section and 1680 mm for the stripping section). This packing material had a specific surface of 500 $m^2/m^3$, a pressure loss of around 2.5 mbar per meter of packing length and a theoretical number of distillation stages of around 6 stages/m. Two falling-film evaporators 6 with evaporator areas of 2.5 and 4.5 $m^2$ operated with liquid circulation and heated with thermal oil were used as "bottom" evaporators.

The second column 3 had a diameter of 316 mm and was equipped with a 4000 mm long, ordered stainless steel packing of the Montz BSH-400 type (2 meters for the concentrating section and 2 meters for the stripping section). This packing material had a specific surface of 400 m$^2$/m$^3$, a pressure loss of around 2.5 mbar per meter of packing length and a theoretical number of distillation stages of around 4 stages/m. A thin layer evaporator with an evaporator area of 1 m$^2$, which was equipped with a wiper with movable wiper blades of the Sambay type and which was heated with thermal oil, was used as the bottom evaporator.

Tube-bundle heat exchangers heated with steam at 42 bar were used as preheaters for both columns while tube bundle heat exchangers cooled with water under pressure were used as condensers. The vacuum was generated at two separate vacuum stations each comprising two steam jet pumps and one water ring pump.

The reaction vessel was a 500 liter stainless-steel stirred tank 8 at atmospheric pressure with a centrifugal pump 11 for circulating the product and was heated with 4 bar steam through its walls. The water required for splitting of the anhydrides was introduced by a membrane metering pump 10.

Example 1 (Comparison Example)

Production of a 91% azelaic acid without anhydride splitting

The test conditions for the production of a 91% azelaic acid are shown in Table 2. The chain distribution of the individual streams is shown in Table 3. This test was carried out without splitting of the anhydrides.

TABLE 2

Test conditions for the production of a 91% azelaic acid without anhydride splitting

| Operational data | First column (1) | Second column (3) |
| --- | --- | --- |
| Feed rate (kg/h) | 60.0 | 48.0 |
| Distillate (kg/h) | 5.4 | 40.7 |
| Bottom product (kg/h) | 54.6 | 7.3 |
| Reflux rate (kg/h) | 123.0 | 5.0 |
| Distillate component (% of feed) | 9.0 | 85.0 |
| Reflux ratio R/D | 22.8 | 0.12 |
| Head pressure (mbar) | 8.0 | 5.5 |
| Bottom pressure (mbar) | 18.4 | 14.5 |
| Head temperature (° C.) | 200.4 | 203.0 |
| Reflux temperature (° C.) | 199.8 | 194.0 |
| Feed temperature (° C.) | 220.5 | 226.8 |
| Bottom temperature (° C.) | 234.4 | Not measured |
| Thermal oil temperature (° C.) | 257.2 | 280.0 |

TABLE 3

Chain distribution of the individual streams in % by weight in the two-stage fractionation of 80% azelaic acid for the production of 91% azelaic acid

| Component | Feed 1st col. | Distillate 1st col. | Bottom 1st col. | Distillate 2nd col. | Bottom 2 2nd col. |
| --- | --- | --- | --- | --- | --- |
| C$_9$ Monocarboxylic acid | 0.17 | 0.30 | 0.05 | — | — |
| <C$_6$ Dicarboxylic acid | 1.15 | 8.70 | 0.13 | — | 0.07 |
| C$_6$ Dicarboxylic acid | 1.80 | 21.85 | — | — | 0.14 |
| C$_7$ Dicarboxylic acid | 2.32 | 28.00 | 0.07 | 0.04 | 0.18 |
| C$_8$ Dicarboxylic acid | 3.55 | 25.23 | 1.72 | 1.94 | 0.46 |
| C$_9$ Dicarboxylic acid | 78.90 | 10.70 | 85.31 | 91.88 | 56.77 |
| C$_{10}$ Dicarboxylic acid | 2.27 | 0.06 | 2.56 | 2.02 | 5.02 |
| C$_{11}$ Dicarboxylic acid | 5.75 | 0.14 | 6.47 | 3.20 | 22.55 |
| C$_{12}$ Dicarboxylic acid | 0.50 | — | 0.57 | 0.16 | 2.56 |

TABLE 3-continued

Chain distribution of the individual streams in % by weight in the two-stage fractionation of 80% azelaic acid for the production of 91% azelaic acid

| Component | Feed 1st col. | Distillate 1st col. | Bottom 1st col. | Distillate 2nd col. | Bottom 2 2nd col. |
| --- | --- | --- | --- | --- | --- |
| >C$_{12}$ Dicarboxylic acid | 0.83 | — | 0.96 | 0.06 | 3.31 |
| Unknowns | 2.76 | 5.02 | 2.16 | 0.70 | 8.94 |

The analysis results were obtained by gas chromatography (GC). The anhydrides are not included because they are split back into the original dicarboxylic acids. However, measurement by NMR spectroscopy revealed a high percentage content, i.e. up to 60% by weight, of anhydrides in the bottom of the second column 3. Accordingly, the distillate component could only be increased to 85% despite the high thermal oil temperature of 280° C. The anhydrides formed are long-chain compounds with high boiling points which do not evaporate at these temperatures.

Example 2

Production of a 91% azelaic acid with anhydride splitting in accordance with the invention In this test, splitting of the anhydrides was integrated into the process. To this end, the bottom product of the first fractionation 1 was treated with water in the following holding tank 8 by the introduction of 2 kg/h of water by the membrane metering pump 10. The test conditions are set out in Table 4.

TABLE 4

Test conditions for the production of a 91% azelaic acid with anhydride splitting

| Operational data | First column (1) | Second column (3) |
| --- | --- | --- |
| Feed rate (kg/h) | 60.0 | 54.0 |
| Distillate (kg/h) | 6.0 | 51.0 |
| Bottom product (kg/h) | 54.0 | 3.0 |
| Reflux rate (kg/h) | 120.0 | 16.0 |
| Distillate component (% of feed) | 10.0 | 94.4 |
| Reflux ratio R/D | 20.0 | 0.31 |
| Head pressure (mbar) | 7.0 | 5.0 |
| Bottom pressure (mbar) | 17.0 | 15.0 |
| Head temperature (° C.) | 204.0 | 200.0 |
| Reflux temperature (° C.) | 198.0 | 185.0 |
| Feed temperature (° C.) | 220.0 | 220.0 |
| Bottom temperature (° C.) | 234.0 | 245.0 |
| Thermal oil temperature (° C.) | 260.0 | 278.0 |

Comparison of Tables 2 and 4 shows that, despite a slightly lower temperature of the thermal oil, approximately 10% more distillate was obtained by splitting of the anhydrides. The product yield of the separation process was thus considerably improved.

The chain distributions of the individual streams obtained in this test are shown in Table 5. The compositions of the end product (distillate second column) and residue (bottom second column) were similar to Example 1, but with a considerably improved product yield in the second fractionating stage.

TABLE 5

Chain distribution of the individual streams in % by weight in the two-stage fractionation of 80% azelaic acid for the production of 91% azelaic acid with splitting of the anhydrides

| Component | Feed 1st col. | Distillate 1st col. | Bottom 1st col. | Distillate 2nd col. | Bottom 2nd col. |
|---|---|---|---|---|---|
| $C_9$ Monocarboxylic acid | 0.17 | 0.21 | — | — | — |
| $<C_6$ Dicarboxylic acid | 1.15 | 8.00 | — | — | — |
| $C_6$ Dicarboxylic acid | 1.80 | 15.35 | 0.11 | — | — |
| $C_7$ Dicarboxylic acid | 2.32 | 16.84 | 0.22 | 0.20 | 0.20 |
| $C_8$ Dicarboxylic acid | 3.55 | 18.12 | 0.75 | 2.70 | 0.50 |
| $C_9$ Dicarboxylic acid | 78.90 | 36.89 | 87.92 | 91.20 | 50.10 |
| $C_{10}$ Dicarboxylic acid | 2.27 | 0.11 | 2.05 | 2.10 | 5.00 |
| $C_{11}$ Dicarboxylic acid | 5.75 | 0.11 | 4.85 | 2.80 | 20.50 |
| $C_{12}$ Dicarboxylic acid | 0.50 | — | 0.22 | 0.20 | 4.40 |
| $>C_{12}$ Dicarboxylic acid | 0.83 | — | 0.43 | 0.10 | 3.90 |
| Unknowns | 2.76 | 4.37 | 3.45 | 0.70 | 15.40 |

The effect of splitting the anhydrides in this test is reflected in the results of an NMR-spectrometric measurement. The bottom product from the first fractionation contained around 13% of anhydrides. After the introduction of water, this figure was reduced to 2.5%. In both cases, the residue of the second fractionation contained around 70% of anhydrides although the quantity of residue was reduced by the addition of water from 15% to 5% of the feed for the fractionation process.

Example 3

Production of a 90% azelaic acid in accordance with the prior art

The 80% azelaic acid obtained by extraction with water and re-extraction of monocarboxylic acids with octane is concentrated to at least 90% in accordance with the prior art by crystallization and filtration and subsequent two-stage distillation of the molten filter cake. Secondary products of this process include the filtrate, normally known as the mother liquor, the distillate of the first distillation (first cut) and the residue of the second distillation (overhead stage).

The compositions of the starting material, the end product and the secondary products are shown in Table 6.

TABLE 6

Chain distribution of the individual streams in % by weight in the concentration of azelaic acid in accordance with the prior art

| Component | Feed | Mother liquor | Distillate | Residue | End product |
|---|---|---|---|---|---|
| $C_9$ Monocarboxylic acid | 0.1 | — | 2.1 | — | — |
| $<C_6$ Dicarboxylic acid | 1.1 | 4.5 | 14.5 | — | — |
| $C_6$ Dicarboxylic acid | 2.2 | 10.5 | 26.1 | — | — |
| $C_7$ Dicarboxylic acid | 2.6 | 14.0 | 27.2 | 0.5 | — |
| $C_8$ Dicarboxylic acid | 4.2 | 25.0 | 30.1 | 1.5 | 0.5 |
| $C_9$ Dicarboxylic acid | 79.0 | 39.0 | — | 49.0 | 89.5 |
| $C_{10}$ Dicarboxylic acid | 2.4 | 5.0 | — | 6.0 | 2.0 |
| $C_{11}$ Dicarboxylic acid | 5.2 | 2.0 | — | 27.0 | 7.0 |
| $C_{12}$ Dicarboxylic acid | 0.5 | — | — | 5.5 | 0.5 |
| $>C_{12}$ Dicarboxylic acid | 0.4 | — | — | 10.5 | 0.5 |
| Unknowns | 2.3 | — | — | — | — |

The quantity balance of the known process is set out in Table 7.

TABLE 7

Quantity balance in the concentration of 80% azelaic acid to 90% in accordance with the prior art

| Product stream | Feed | Mother liquor | Distillate | Residue | End Product |
|---|---|---|---|---|---|
| Mass flow (%) | 100 | 9.0 | 2.8 | 6.4 | 81.8 |

The quantity balance and the compositions of the individual streams show an azelaic acid yield of 93% and a total product yield of 82% for the known process. By contrast, the yield of azelaic acid in the process according to the invention is 98% and the total product yield 85%.

| List of Reference Numerals | |
|---|---|
| 1 | First fractionating column, first process step |
| 2 | Reaction stage, second process step |
| 3 | Second fractionating column, third process step |
| 4 | Mass transfer packing |
| 5 | First runnings |
| 6 | Falling-film evaporator |
| 7 | Pump |
| 8 | Holding tank |
| 9 | Tank |
| 10 | Pump |
| 11 | Forced circulation |
| 12 | Pump |
| 13 | Mass transfer packing |
| 14 | Residue |
| 15 | Distillate |
| 16 | Flaking roller |
| 17 | Thin-layer evaporator. |

We claim:

1. A process for the production of purified azelaic acid by working up a reaction mixture containing $C_{1-18}$ monocarboxylic acids, comprising pelargonic acid, and $C_{4-16}$ dicarboxylic acids, comprising azelaic acid, obtained from the ozonolysis of oleic acid or a starting mixture containing oleic acid, all but <2% by weight of the monocarboxylic acids and part of the dicarboxylic acids with a chain length of $<C_9$ and $>C_9$ being separated off to obtain a prepurified product containing more than 75% by weight of oleic acid and the prepurified product being concentrated to more than 90% by weight of oleic acid in several process steps of which the last is an overhead distillation step, which comprises: (1), removing the dicarboxylic acids with chain lengths of $<C_9$, present in the prepurified product, as an overhead product by a first fractional distillation; (2), reacting a bottom product from the first distillation with water to split carboxylic anhydrides present in the bottom product to form a reaction mixture and, (3), distilling the reaction mixture to recover as an overhead product the purified azelaic acid, the third process step (3) being carried out after or at the same time as the second process step (2).

2. The process as claimed in claim 1, wherein process steps (1) and (3) are each carried out in a fractionating column under a head pressure of 1 to 30 mbar.

3. The process as claimed in claim 1 wherein a falling-film evaporator is used as the bottom heater in the fractionating column for the first process step (1).

4. The process as claimed in claim 1 wherein a bottom heater in the third step distillation is selected from the group consisting of a wiped-film evaporators and falling-film evaporators.

5. The process as claimed in claim 1 wherein the second process step (2) is carried out in a stirred tank reactor, or in a static mixer.

6. The process as claimed in claim 1 wherein the bottom product obtained in the first process step (1) is fed directly into a third step fractionating column and, steam is introduced into the column to carry out the second process step.

7. The process as claimed in claim 6, wherein the bottom product obtained in the first process step (1) is introduced approximately in the middle of the third step fractionating column while superheated steam, is introduced into an evaporator of the third step fractionating column.

8. The process as claimed in claim 2 wherein a falling-film evaporator is used as the bottom heater in the fractionating column for the first process step (1).

9. The process as claimed in claim 2 wherein a bottom heater in the third step distillation is selected from the group consisting of a wiped-film evaporators and falling-film evaporators.

10. The process as claimed in claim 2 wherein the second process step (2) is carried out in a stirred tank reactor, or in a static mixer.

11. The process as claimed in claim 2 wherein the bottom product obtained in the first process step (1) is fed directly into a third step fractionating column and, steam is introduced into the column to carry out the second process step.

12. The process as claimed in claim 11, wherein the bottom product obtained in the first process step (1) is introduced approximately in the middle of the third step fractionating column while superheated steam, is introduced into an evaporator of the third step fractionating column.

13. The process as claimed in claim 3 wherein a bottom heater in the third step distillation is selected from the group consisting of a wiped-film evaporators and falling-film evaporators.

14. The process as claimed in claim 3 wherein the second process step (2) is carried out in a stirred tank reactor, or in a static mixer.

15. The process as claimed in claim 3 wherein the bottom product obtained in the first process step (1) is fed directly into a third step fractionating column and, steam is introduced into the column to carry out the second process step.

16. The process as claimed in claim 15, wherein the bottom product obtained in the first process step (1) is introduced approximately in the middle of the third step fractionating column while superheated steam, is introduced into an evaporator of the third step fractionating column.

17. The process as claimed in claim 4 wherein the second process step (2) is carried out in a stirred tank reactor, or in a static mixer.

18. The process as claimed in claim 4 wherein the bottom product obtained in the first process step (1) is fed directly into a third step fractionating column and, steam is introduced into the column to carry out the second process step.

19. The process as claimed in claim 18, wherein the bottom product obtained in the first process step (1) is introduced approximately in the middle of the third step fractionating column while superheated steam, is introduced into an evaporator of the third step fractionating column.

20. The process as claimed in claim 5 wherein the bottom product obtained in the first process step (1) is fed directly into a third step fractionating column and, steam is introduced into the column to carry out the second process step.

21. The process of claim 1 wherein the azelaic acid is obtained from ozonolysis of oleic acid without a prior crystallization step.

22. In a process for recovery of azelaic acid wherein azelaic acid is heated during the process and a composition containing a high boiling point anhydride of azelaic acid is formed, the improvement which comprises: contacting the composition with water or steam to form a mixture containing azelaic acid and a reduced content of the anhydride of azelaic acid and recovering at least a portion of the azelaic acid.

23. The process of claim 22 wherein the azelaic acid is recovered by distillation.

24. The process of claim 22 wherein the composition containing the anhydride of azelaic acid is formed in the reboiling section of a distillation column.

* * * * *